(12) United States Patent
Lab et al.

(10) Patent No.: US 12,196,732 B2
(45) Date of Patent: Jan. 14, 2025

(54) MANUFACTURING TEST BLOCK

(71) Applicant: The Truth 3DP Technologies LLC, Louisville, OH (US)

(72) Inventors: Tyler Andrew Lab, Louisville, OH (US); Greg Clark, Louisville, OH (US)

(73) Assignee: The Truth 3DP Technologies LLC, Louisville, OH (US)

( * ) Notice: Subject to any disclaimer, the term of this patent is extended or adjusted under 35 U.S.C. 154(b) by 493 days.

(21) Appl. No.: 17/330,483

(22) Filed: May 26, 2021

(65) Prior Publication Data
US 2022/0381757 A1 Dec. 1, 2022

(51) Int. Cl.
*G01N 33/02* (2006.01)
*G01N 27/00* (2006.01)
*G01N 35/04* (2006.01)

(52) U.S. Cl.
CPC ............. *G01N 33/02* (2013.01); *G01N 27/00* (2013.01); *G01N 2035/0432* (2013.01)

(58) Field of Classification Search
CPC ............................. G01N 33/02; G01N 27/00
See application file for complete search history.

(56) References Cited

FOREIGN PATENT DOCUMENTS

| CN | 204924886 U | * | 12/2015 |
|---|---|---|---|
| CN | 107782860 A | * | 3/2018 |
| CN | 110632417 A | * | 12/2019 |
| CN | 216050354 U | * | 3/2022 |

* cited by examiner

*Primary Examiner* — Jamel E Williams
(74) *Attorney, Agent, or Firm* — Sand, Sebolt & Wernow Co., LPA

(57) ABSTRACT

The present disclosure provides a device and method of operation thereof relating to a manufacturing test block with a plug that has a contaminant within the plug. The manufacturing test block contains a plurality of apertures and a plug with a contaminant within it that is to be sensed by a detector. Specifically, the present disclosure relates to a manufacturing test block that is customizable in shape to a customer's needs that can be placed on a conveyor system in order to test for contaminants within the conveyor line full of packaged products while not interrupting the other packages.

20 Claims, 8 Drawing Sheets

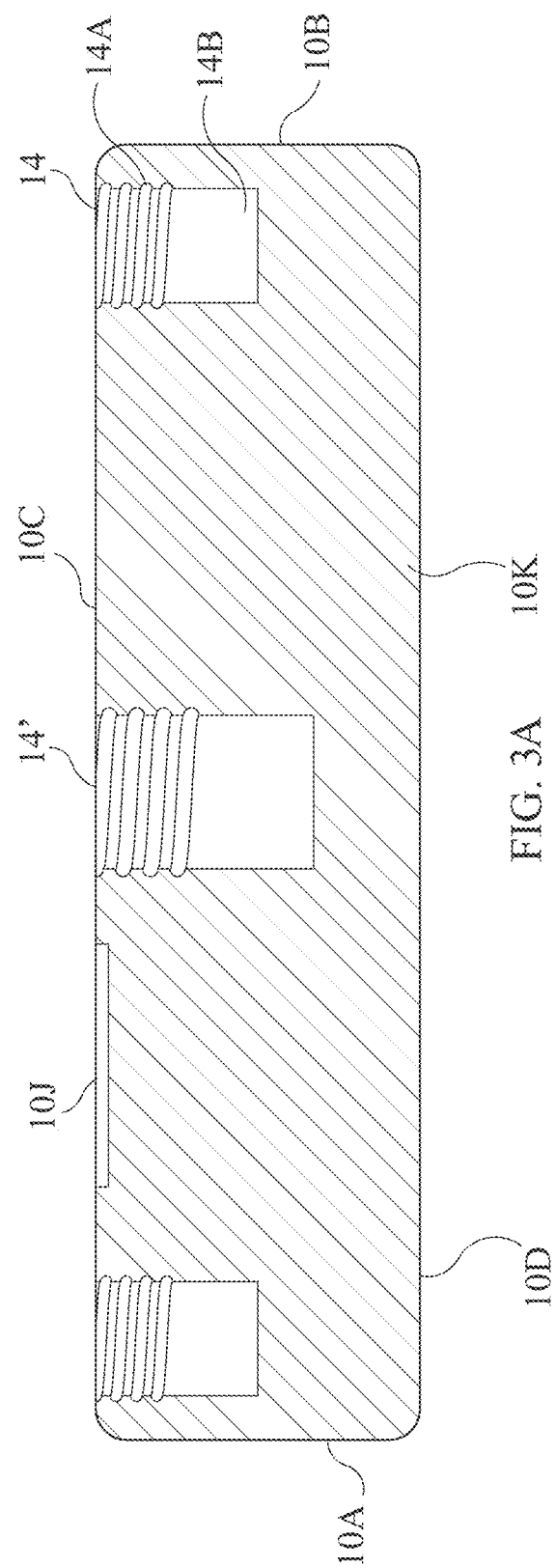

MANUFACTURING TEST BLOCK

TECHNICAL FIELD

This disclosure is directed generally to a manufacturing test block with a plug that has a contaminant within the plug. More particularly, the present disclosure relates to a manufacturing test block with a plurality of apertures and a plug with a contaminant within it that is to be sensed by a detector. Specifically, the present disclosure relates to a manufacturing test block that is customizable in shape to a customer's needs that can be placed on a conveyor system in order to test for contaminants within the conveyor line full of packaged products while not interrupting the other packages.

BACKGROUND

Background Information

In the food industry, metal detectors play a vital role. In the past, many pieces of metal originating from a conveyor system, metal shavings, or pieces of metal have been found in food products. The presence of these contaminants went unnoticed during inspection and necessitated expensive food recalls.

Therefore, it is common to use a metal detection apparatus to detect and reject unwanted metal contamination. When properly installed and operated, the metal detection apparatus will help by reducing metal contamination and improving food safety. The metal detection apparatus typically comprises a metallic enclosure, having entrance and exit apertures with cross-sectional areas of different or equal size defining a travel path inside the enclosure along which an object under inspection moves.

As a particle of metal passes through the metal detection apparatus, a high frequency field is disturbed. This disturbance results in a signal that can be amplified, processed, and subsequently be used to detect the presence of the metal contamination.

Further in the food industry, testing the metal detection apparatus can be problematic. It is common to use a test device such as cards or sticks containing a piece of metal that is placed onto the top of a package on the conveyor system. When the test device is placed onto the package, the package is moving rather quickly on the conveyor line. This can lead the device to fall off the package or move unpredictably during its journey. Additionally, if the device is a specific color or shape, certain testing may remove the package because of this reason, rather than the device containing metal.

SUMMARY

Therefore, devices to test metal detectors can benefit from improvement.

In one aspect, an exemplary embodiment of the present disclosure may provide a manufacturing test block comprising: a body with a height, width, and depth; at least one aperture located on a side of the body; at least one plug adapted to interface with the at least one aperture; and at least one test piece within the plug adapted to be detected by a detector. This exemplary embodiment or another exemplary embodiment may further provide for the body comprises at least one of the following: acrylonitrile butadiene styrene (ABS), polylactic acid (PLA), acrylonitirle styrene acrylate (ACA), polyethylene terephthalate (PET), glycolized polyester (PETG), polycarbonate (PC), polyetherimide (PEI), polyaryletherketone (PAEK), polyether ether ketone (PEEK), polyetherketoneketone (PEKK), polyphenylsulfone (PPSU), polypropylene (PP), polyamides (nylon), thermoplastic polyurethane (TPU), composite materials, and hybrid materials. This exemplary embodiment or another exemplary embodiment may further provide for the at least one plug comprises at least one of the following: acrylonitrile butadiene styrene (ABS), polylactic acid (PLA), acrylonitirle styrene acrylate (ACA), polyethylene terephthalate (PET), glycolized polyester (PETG), polycarbonate (PC), polyetherimide (PEI), polyaryletherketone (PAEK), polyether ether ketone (PEEK), polyetherketoneketone (PEKK), polyphenylsulfone (PPSU), polypropylene (PP), polyamides (nylon), composite materials, and hybrid materials. This exemplary embodiment or another exemplary embodiment may further provide for the at least one test piece comprises at least one of the following: chrome steel, brass, stainless steel, titanium, phosphor bronze, and aluminum. This exemplary embodiment or another exemplary embodiment may further provide for the at least one test piece comprises at least one of the following: ceramic, soda lime glass, borosilicate glass, crystal glass, polytetrafluoroethylene, nylon, and nitrile. This exemplary embodiment or another exemplary embodiment may further provide for the at least one plug is in removable engagement aperture of the body. This exemplary embodiment or another exemplary embodiment may further provide for the at least one plug has a graspable portion. This exemplary embodiment or another exemplary embodiment may further provide at least one aperture is located on a top side of the body and at least one aperture is located on a different side of the body. This exemplary embodiment or another exemplary embodiment may further provide the at least one aperture has at least one depth into the body of the test block. This exemplary embodiment or another exemplary embodiment may further provide at least one of the at least one aperture has a first diameter and at least one of the aperture has a second diameter.

In another aspect, an exemplary embodiment of the present disclosure may provide a method for testing for a contaminant comprising: placing a test piece containing the contaminant desired to be tested for in a plug; installing the plug in a device; passing the device through a detector operative to detect the contaminant; and detecting the contaminant with the detector. This exemplary embodiment or another exemplary embodiment may further provide for removing the plug; installing a second plug within the device with a second contaminant desired to be tested for in the second plug; passing the device through the detector operative to detect the second contaminant; and detecting the second contaminant with the detector. This exemplary embodiment or another exemplary embodiment may further provide for moving the plug from a first location on the device to a further location on the device; passing the device through a detector operative to detect the contaminant; and detecting the contaminant with the detector. This exemplary embodiment or another exemplary embodiment may further provide for iteratively moving the plug in order to detect containments at any location within the device or surrounding areas. This exemplary embodiment or another exemplary embodiment may further provide for customizing the shape of the device. This exemplary embodiment or another exemplary embodiment may further provide for changing the dimensions of the device to result in a second device; installing the plug in the second device; passing the second device through the detector; and detecting the contaminant with the detector. This exemplary embodiment or another exemplary embodiment may further provide for prior to passing further comprising: placing the device on a conveyor system. This exemplary embodiment or another exemplary embodiment may further provide for installing at least one second plug within the device with at least one second contaminant.

In another aspect, an exemplary embodiment of the present disclosure may provide placing a test piece containing a contaminant desired to be tested for in a plug; installing the plug in a first aperture in a device; passing a device through a detector operative to detect the contaminant; detecting the contaminant with the detector; removing the plug from the first aperture; installing the plug in a second aperture; and passing the device through the detector operative to detect the contaminant. In another aspect, an exemplary embodiment of the present disclosure may provide iteratively moving the plug in order to detect containments at any location within the device. In another aspect, an exemplary embodiment of the present disclosure may provide removing the plug; installing a second plug within the device with a second contaminant desired to be tested for in the second plug; passing the device through the detector operative to detect the second contaminant; and detecting the second contaminant with the detector. In another aspect, an exemplary embodiment of the present disclosure may provide customizing the shape of the device. In another aspect, an exemplary embodiment of the present disclosure may provide placing the device on a conveyor system.

BRIEF DESCRIPTION OF THE SEVERAL VIEWS OF THE DRAWINGS

Sample embodiments of the present disclosure are set forth in the following description, are shown in the drawings, and are particularly and distinctly pointed out and set forth in the appended claims.

FIG. 3A is a cross sectional view of an alternative embodiment of an exemplary manufacturing test block with plugs removed, taken along line 3-3 of FIG. 2.

Similar numbers refer to similar parts throughout the drawings.

DETAILED DESCRIPTION

A new device 10, method of operation thereof and method of fabrication thereof, is depicted in the present disclosure and throughout FIGS. 1-9. Device 10 is a new and improved manufacturing test block for use with a piece of scanning equipment, namely a metal detector, as will be discussed hereafter.

Figure 1:
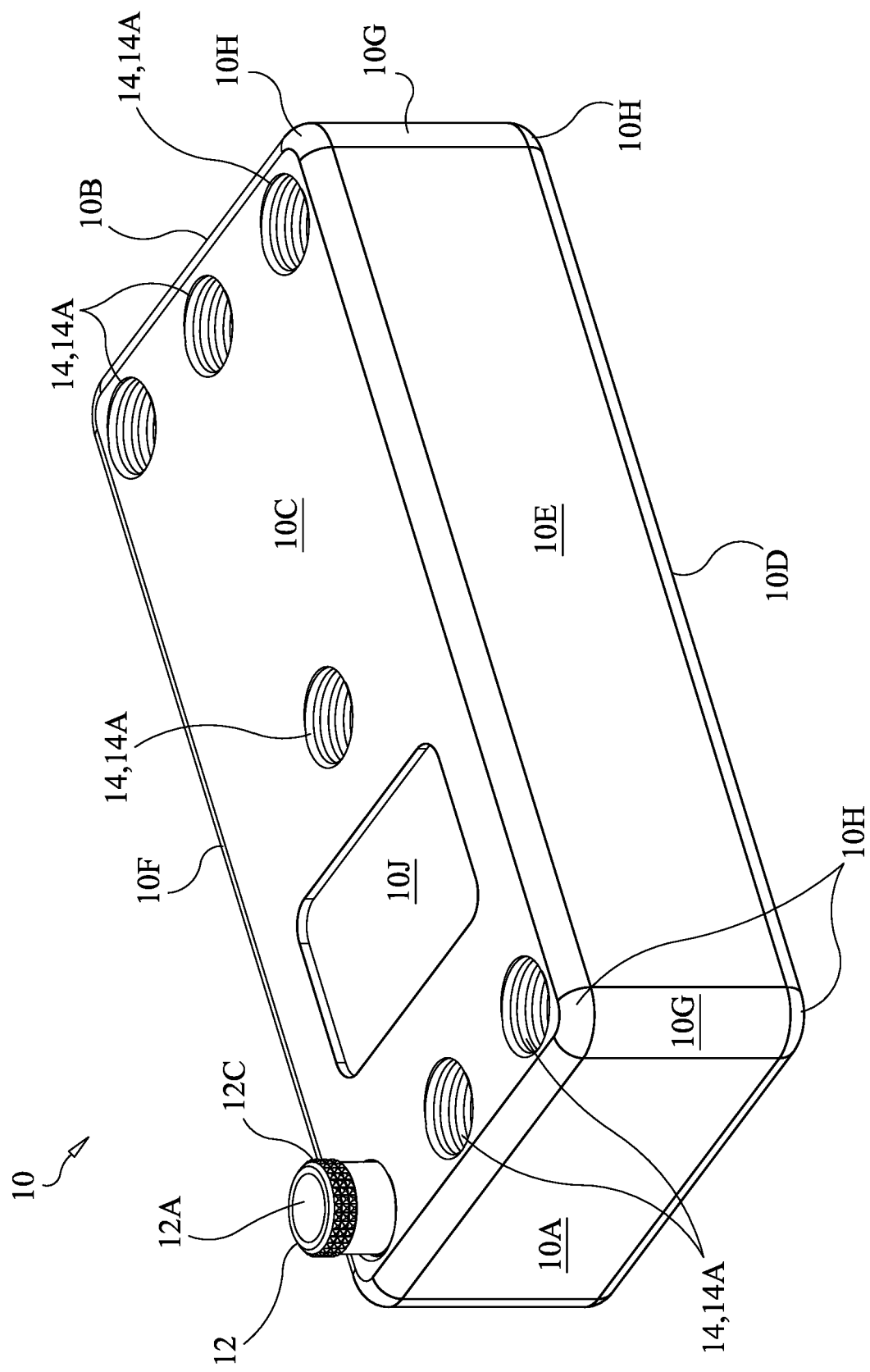
FIG. 1 is a top right side perspective view of an exemplary manufacturing test block with one plug installed.
Figure 2:
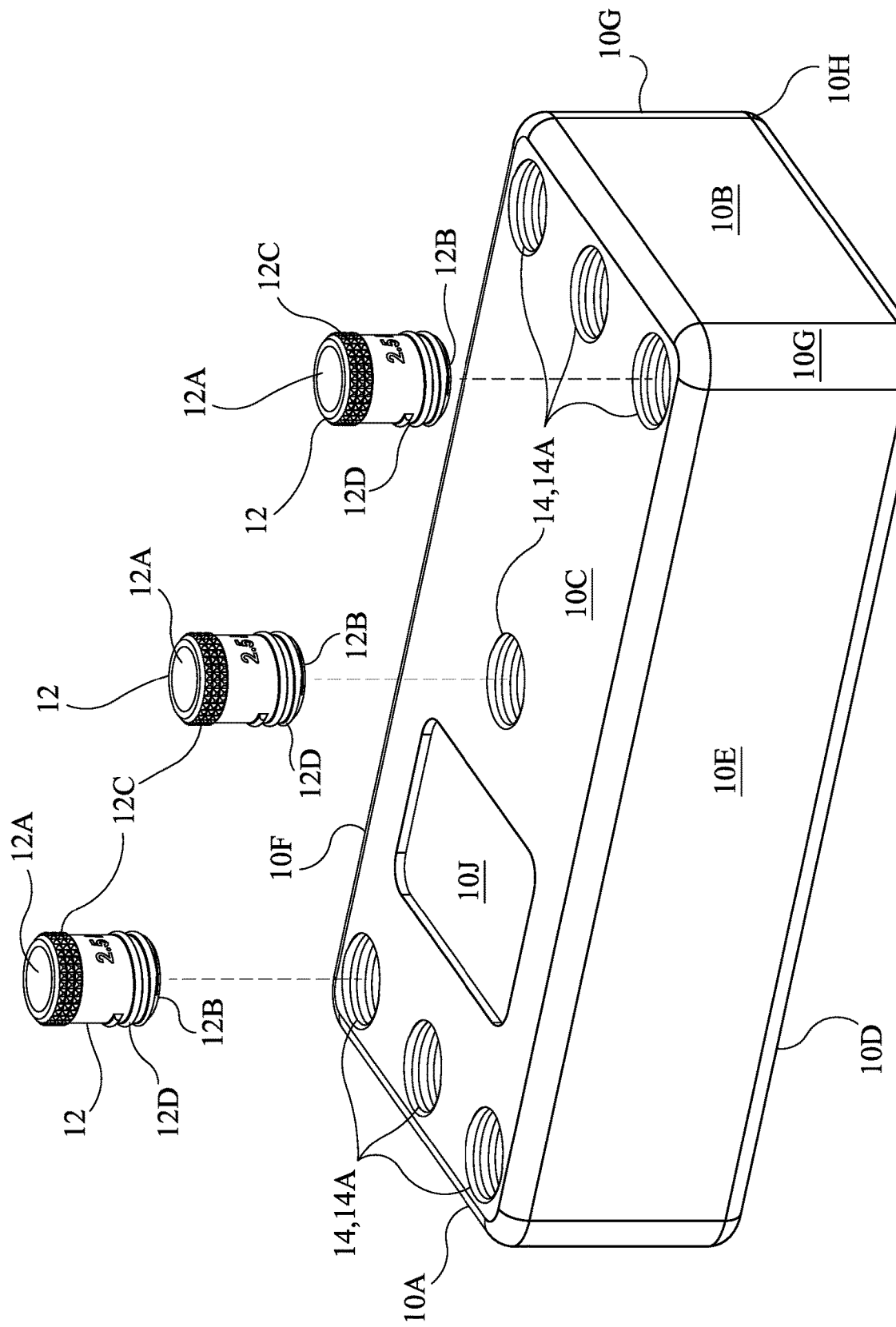
FIG. 2 is a top left side partially exploded perspective view of the exemplary manufacturing test block with plugs removed.

Referring specifically to FIG. 1 and FIG. 2, a top right side and top left side perspective view, respectfully, of an exemplary manufacturing test block device 10 with at least one plug 12 installed (in FIG. 1) or exploded away (in FIG. 2) is shown. The exemplary device 10 includes a body that is generally rectangular in nature. Device 10 including a first end 10A, a second end 10B longitudinally disposed to the first end 10A. The exemplary device 10 further includes a top side 10C, a bottom side 10D vertically opposed from the top side 10C. Additionally, the device 10 has a first side 10E and a second side 10F transversely opposed from the first side 10E. In the exemplary shown device 10, between the first side 10E and the first end 10A is a rounded portion 10G that connects the first side 10E with the first end 10A that is generally convex in nature. Further, there are additional rounded portions 10G that connect the first side 10E with the second end 10B, the second side 10F with the first end 10A, and the second side 10F with the second end 10B. Further, the exemplary device 10 may include a beveled region 10H that tapers and spans between the top side 10C and portions of the first end 10A, second end 10B, first side 10E, and second side 10F, respectfully. There may be an additional beveled region 10H that tapers and spans between the bottom side 10D and portions of the first end 10A, second end 10B, first side 10E, and second side 10F, respectfully.

Additionally, the device 10 includes a depression 10J. In the depression identifying indicia may be present as will be discussed with respect to operation. Further, the device 10 has a given height H1, width W1 and depth D1. While this device 10 is shown generally and as an exemplary embodiment as a cuboid shape, as will be discussed later with respect to fabrication, the height, width, and depth, could all be modified as required. Further, in alternative embodiments non-cuboid shapes could be used such as variations on prisms, cylinders and other similar shapes.

The at least one plug 12 has a top side 12A and a bottom side 12B vertically opposed from the top side 12A. Proximate the top side 12A is an outer graspable surface 12C. While in the shown embodiment the graspable surface 12C is knurled, one skilled in the art will understand this to be one of many desired implementations. For example, alternative embodiments may have a recessed portion to allow for grasping of a user, or may have a winged outer portion in order to turn the plug. Proximate the bottom side 12B is a engagable surface 12D. Also included on the plug 12 are identifying indicia 12E. These indicia 12E identify the type of plug 12, as will be discussed with respect to FIG. 4 and FIG. 5

Further included in the top side 10C are a plurality of apertures 14. A set of apertures 14 are proximate the first end 10A, while another set of apertures 14 are proximate the second end 10B, while a single aperture 14 is between the first end 10A and the second end 10B. While the number of apertures 14 in the exemplary embodiment is three proximate the first end 10A, three proximate the second end 10B, and a single aperture 14 is between the first end 10A and the second end 10B, this is merely exemplary. In other embodiments any configuration of apertures can be used, as will be discussed further with respect to operation. Further, in alternative embodiments the apertures may have different depths, dimensions and/or locations depending on the desired implementation. For example, there may be additional apertures located in different sides of the device 10 in alternative embodiments including the first end 10A, second end 10B, bottom side 10D, first side 10E or second side 10F.

In the exemplary embodiment of the device 10, the apertures 14 possess a matable surface 14A. The matable surface 14A is complementary to the engagable surface 12D of the plug 12. While the exemplary embodiment of the engagable surface 12D of the plug 12 are threads and the matable surface 14A are recesses to accept the threads, one skilled in the art will understand this to be one of many desired implementations and is not limited. In alternative embodiments, there may be any securement mechanism to secure the plug 12 within the aperture 14 such as snaps, clips, and other mechanisms of the like. In an alternative embodiment, the matable surface 14A or the engagable surface 12D may be covered with an adhesive and this thereby affixes the plug 12 to the device 10.

Figure 3:
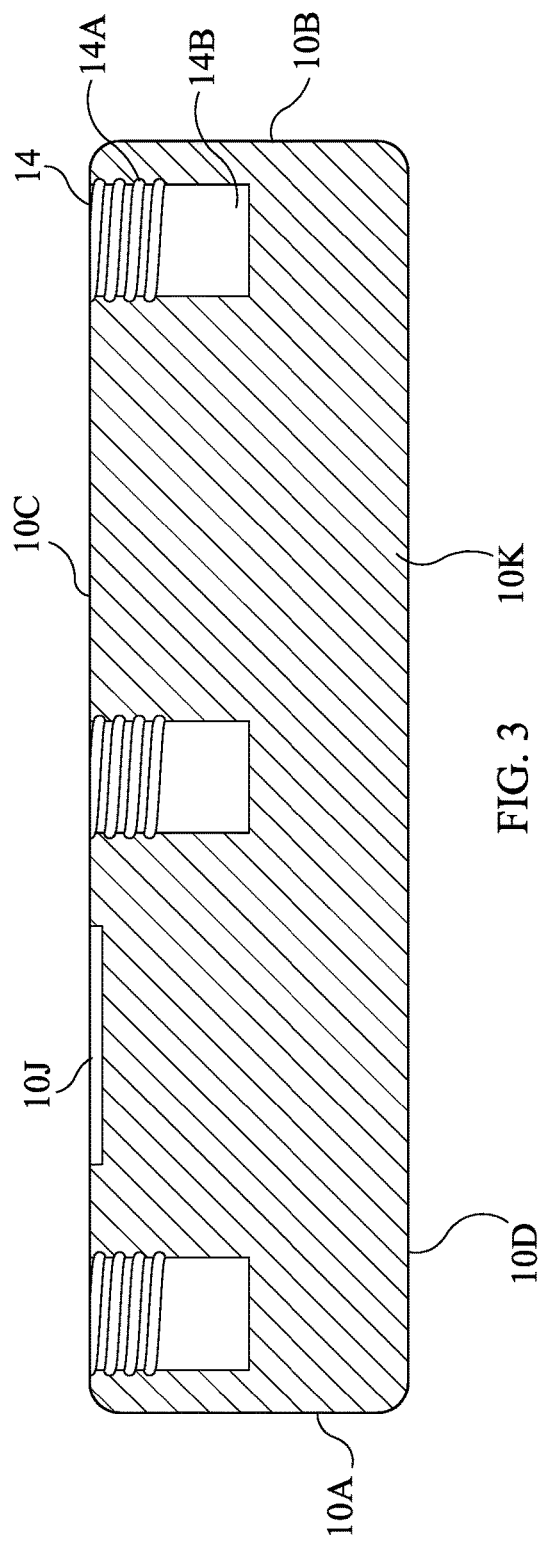
FIG. 3 is a cross sectional view along line 3-3 of FIG. 2.

Referring specifically to FIG. 3, a cross sectional view along line 3-3 of FIG. 2, is shown. In this view, one may see the matable surface 14A of the apertures 14. Vertically below the matable surface 14A is a smooth surface 14B. One may understand that with the matable surface 14A being complementary to the engagable surface 12D of the plug 12 the matable surface may extend more or less depending on the desired implementation. Further the distance D2 of the depth of the aperture 14 may depend on the desired implementation.

FIG. 3A shows a cross sectional view of an alternative embodiment of an exemplary manufacturing test block with plugs removed. In this alternative embodiment, at least one of the apertures 14 is of a first diameter and depth that is substantially identical to the apertures 14 shown in FIG. 3. However, FIG. 3A also shows another of the apertures, namely aperture 14', having a second diameter and a second depth, where the second diameter and the second depth differ from the diameter and depth of the apertures 14. It will be understood that a plug complementary in dimensions to aperture 14' will be selectively engageable in the aperture 14'.

Further seen in this view is the interior 10K of the device 10. The interior of the device may be solid, may be hollow, or may be some combination thereof. Further, the interior 10K may be filled with a separate material depending on the desired implementation as will be discussed with respect to operation.

Figure 5:
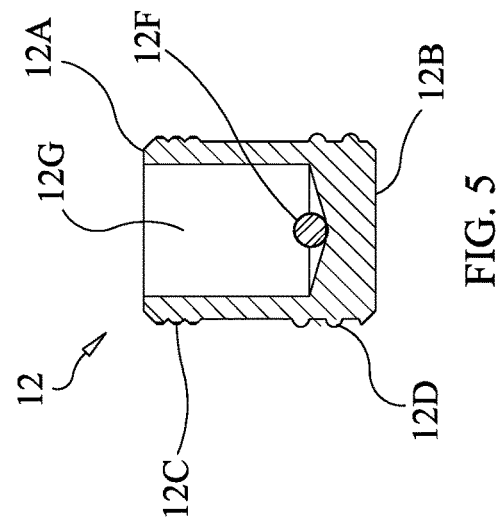
FIG. 5 is a cross sectional view of an exemplary plug.
Figure 4:
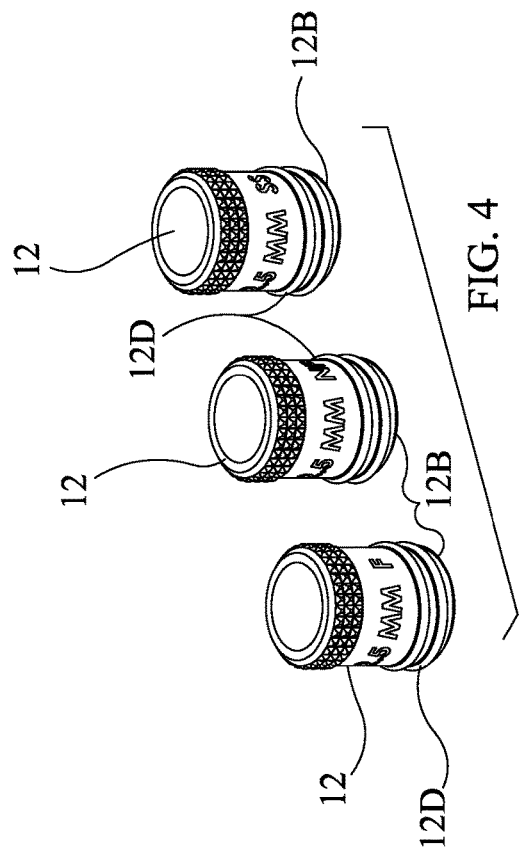
FIG. 4 is a top right perspective view of a plurality of plugs.

Referring specifically to FIG. 4 and FIG. 5, exemplary plugs are shown. Exemplary plugs 12 include a test piece 12F as seen in cross section of FIG. 5. The indicia 12E identify the type of test piece 12F embedded in the plug 12. Generally, the indicia will include the size of the test piece 12F as well as the material which the test piece 12F is composed.

Common indicators for the test piece 12F include "F" for Ferrous or chrome steel, "NF" for Non-Ferrous, generally brass, and "SS" for grade 316 stainless steel. These are three metal options designed to be used in conjunction with a metal detector, but are not limited to merely these three. Other examples may include, but are not limited to grade 304 stainless steel, grade 420 stainless steel, grade 440C stainless steel, titanium, phosphor bronze or aluminum. Further, in other situations, a non-metal substance or other contaminant may be used in order to be used in conjunction with an X-ray machine or other such similarly situated device. In that instance, the test piece 12F may include but is not limited to, ceramic, soda lime glass, borosilicate glass, crystal glass, polytetrafluoroethylene, nylon, and/or nitrile. The interior 12G of the plug 12 may be hollow, solid, filled with a different material, or some combination in between.

The size of the test piece 12F are dependent on the product, testing method sensitivity, and the test piece 12F composition. In some embodiments the test piece is spherical and between about 1 mm and about 10 mm in diameter. In other embodiments, the test piece is between about 2 mm and about 8 mm in diameter. In yet additional embodiments, the test piece is about 2.5 mm and about 6 mm in diameter. In further embodiments, there may be more than one test piece 12F located within the plug 12.

Having described the device, an exemplary method of manufacture will be described. A customer will approach with a specific package design and materials and methods of testing for those materials. This specific package design will contain the dimensions of the package itself, along with the weight of the package. The device 10 may then be fabricated with these dimensions and weight in mind. The plugs 12 are manufactured to contain the desired test material. The weight of the plugs 12 may be subtracted from the weight of the specific package design in order to obtain the weight of the device 10. Knowing the desired weight of the device 10, the device may be fabricated out of a number of food safe materials with varying densities while also being fabricated in a way to vary the density. In one embodiment computer assisted software may enable the optimal fabrication design when input to specific parameters including the height, width, depth of the device 10 along with the materials it is to be made of and any relevant densities.

In one embodiment, the device 10 may be constructed by a 3D printer. Suitable materials or mixtures of materials may include, but are not limited to acrylonitrile butadiene styrene (ABS), polylactic acid (PLA), acrylonitirle styrene acrylate (ACA), polyethylene terephthalate (PET), glycolized polyester (PETG), polycarbonate (PC), polyetherimide (PEI), polyaryletherketone (PAEK), polyether ether ketone (PEEK), polyetherketoneketone (PEKK), polyphenylsulfone (PPSU), polypropylene (PP), polyamides (nylon), thermoplastic polyurethane (TPU), composite materials, and hybrid materials. In other embodiments, the device 10 could be constructed by blow molding, injection molding, rotational molding, compression molding, and/or thermoforming.

Figure 6:
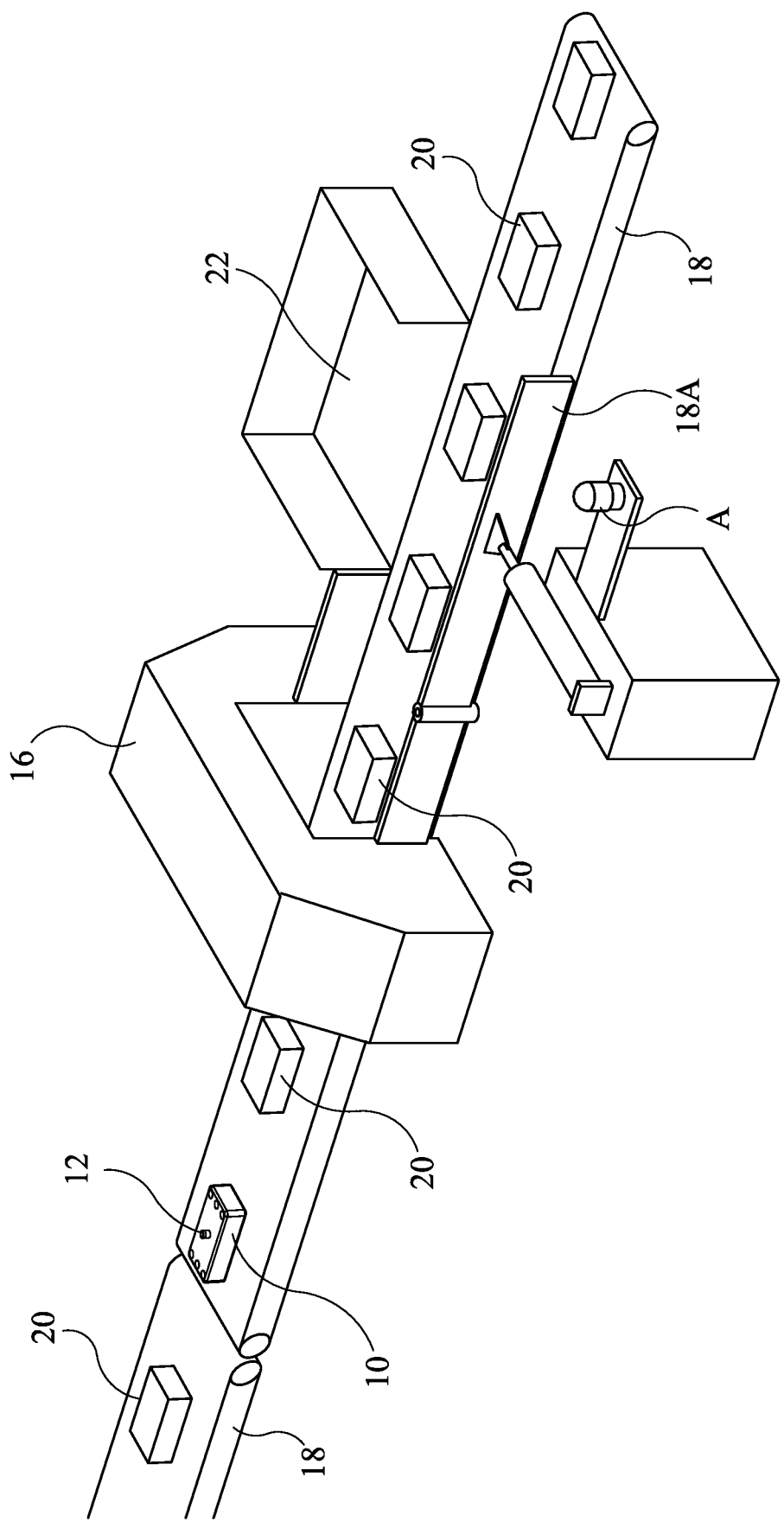
FIG. 6 is an operational view of an assembly line with the exemplary manufacturing test block as one of many packages on the line.

Once the device 10 is made with at least one corresponding plug 12, the device 10 may be tested in conjunction with its detector. In the case of metal, that would be a metal detector. Alternatively, in the case of glass, that could be an x-ray machine and subsequent detector 16. Referring specifically to FIG. 6, an operational view of an assembly line 18 with the exemplary manufacturing test block 10 with a plug 12 installed as one of many normal packages 20 on a conveyor belt line 18. Prior to this, the customer has provided specifications for the dimensions and weight for the device 10, as well as the material choice and size desired to be tested for that has been placed within the plug 12. The plug 12 has been placed into the aperture 14 and secured to the device 10 through the interface of the matable surface 14A on the aperture 14 and the engagable surface 12D of the plug 12.

Figure 7:
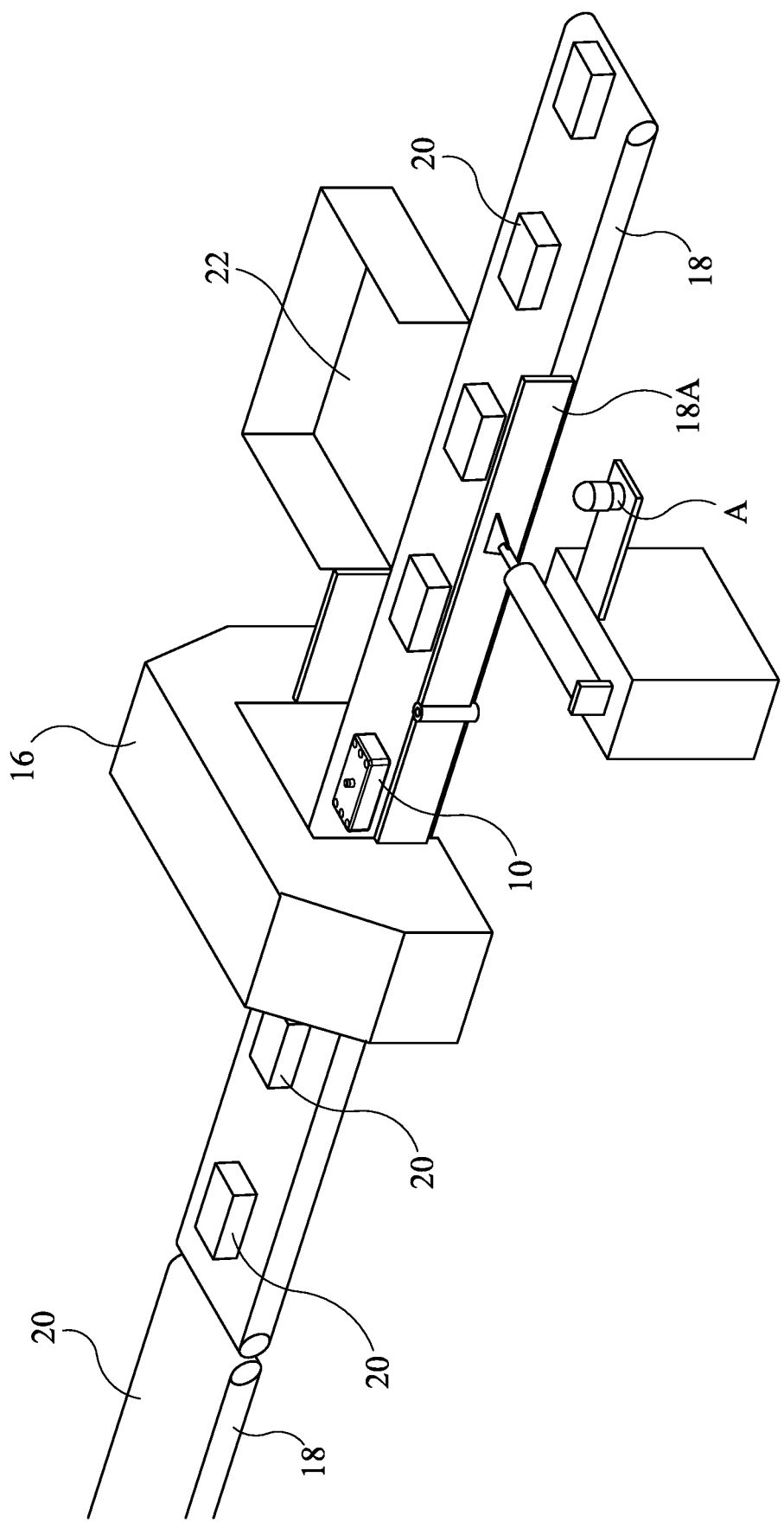
FIG. 7 is a further operational view of the assembly line with the exemplary manufacturing test block having passed under a piece of scanning equipment.

Referring specifically to FIG. 7 a further operational view of the assembly line 18 with the exemplary manufacturing test block 10 being passed under a detector 16 is shown. As the plug 12 has been doped with a contaminant in the form of the test piece 12F, the detector 16 should recognize this is a contaminant and prepare to divert the test block 10. In the illustrated embodiment, it is shown to be in the aperture 14 near the center of the device 10 between the first end 10A and second end 10B and first side 10E and second side 10F.

Different package sizes and different detectors have different sweep patterns. These sweep patterns are the way that the detector "sweeps" its scan across a package in order to properly scan for contaminants. In some instances, the sweep may be mistimed or ill-timed so as to miss contaminants by not scanning the entirety of the package. Unfortunately, prior art designs are poorly equipped in order to determine the sweep pattern effectiveness. Instead, recalls occur after the fact, or timely and error prone visual inspections must be done.

The device 10 allows the removal of the plug 12 from a first aperture 14 and placed into a second aperture 14. As a result of this movement, the device 10 could be added to the assembly line in an iterative manner. Namely, one could add the device to the assembly line 18 with the plug 12 installed in each aperture 14 located on the device to make sure that the detector 16 is scanning the other packages properly. The plug 12 could be placed in any aperture 14. In an exemplary embodiment, the plug would move between aperture 14 near the center of the device 10 between the first end 10A and second end 10B and first side 10E and second side 10F, to an aperture along the top side 10C proximate the first side 10E, then to another aperture along the top side 10C proximate the first side 10E and first end 10A. The plug 12 may then continue to move along the top side 10C to other apertures including the proximate the first side 10E and second end 10B, then proximate the second side 10F and first end 10A and finally proximate the second side 10F and second end 10B. This is merely exemplary movement and the movement may occur in any manner. Further, this is but one exemplary embodiment and depending on the ultimate shape of the device 10, additional apertures and/or apertures in different locations may be required in the desired implementation.

Figure 8:
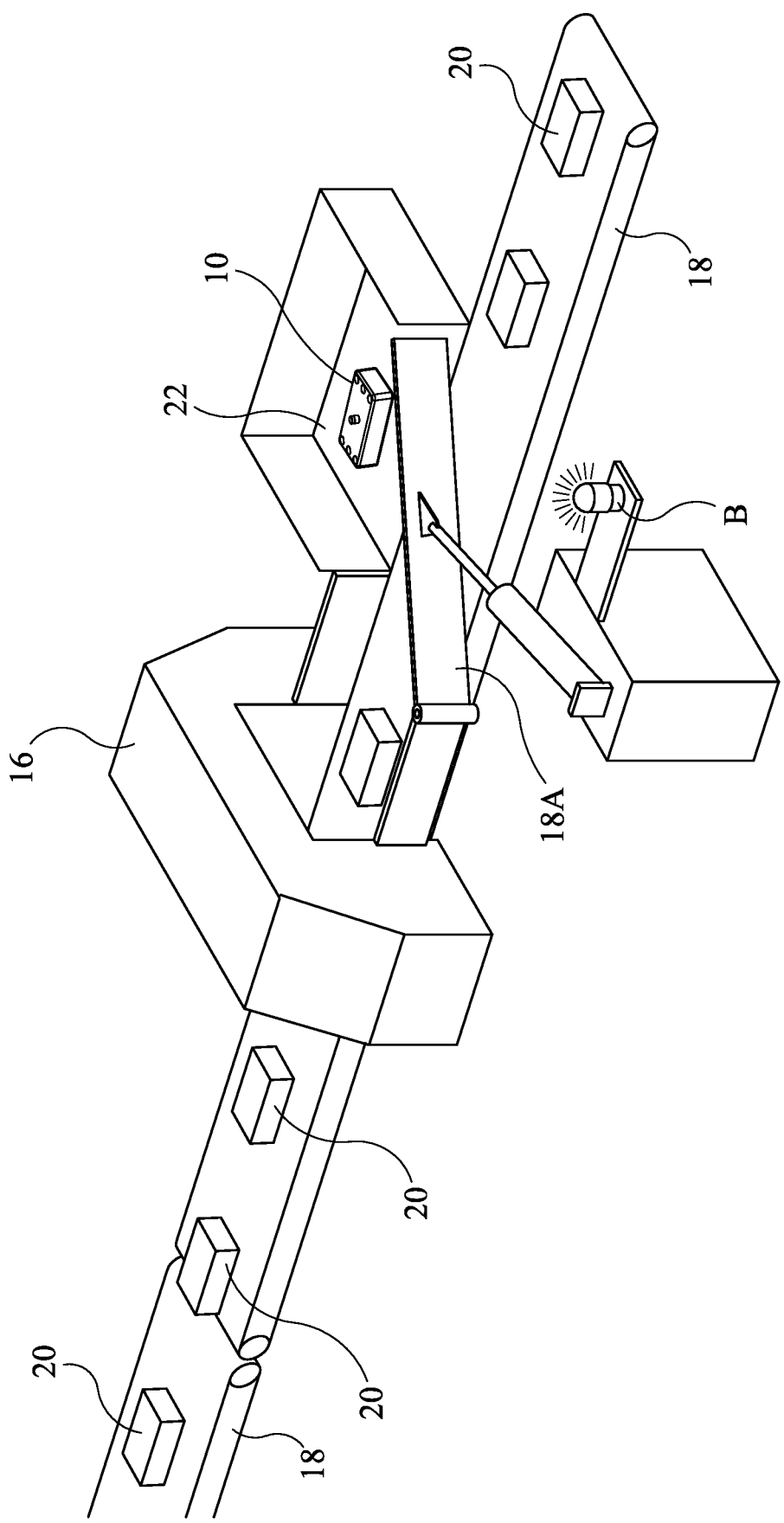
FIG. 8 is another further operational view of the assembly line with the exemplary manufacturing test block having been removed from the flow of the line.

Referring specifically to FIG. 8, another further operational view of the assembly line 18 with the exemplary manufacturing test block 12 having been removed from the flow of the line 18 is shown. In the instance that the detector 16 detects the plug 12 with the test piece 12F inside of it, the detector 16 will cause an alert, in at least one of an audible noise or light changing from "A" to "B" and promptly remove the device 10 from the flow of the assembly line 18 by any known method. In the exemplary example, this may be a kickoff arm 18A into a rejected area 22. As the detector 16 has been previously calibrated as described above, it will not accidently remove other packages from the line, or miss detecting the test piece 12F.

Figure 9:
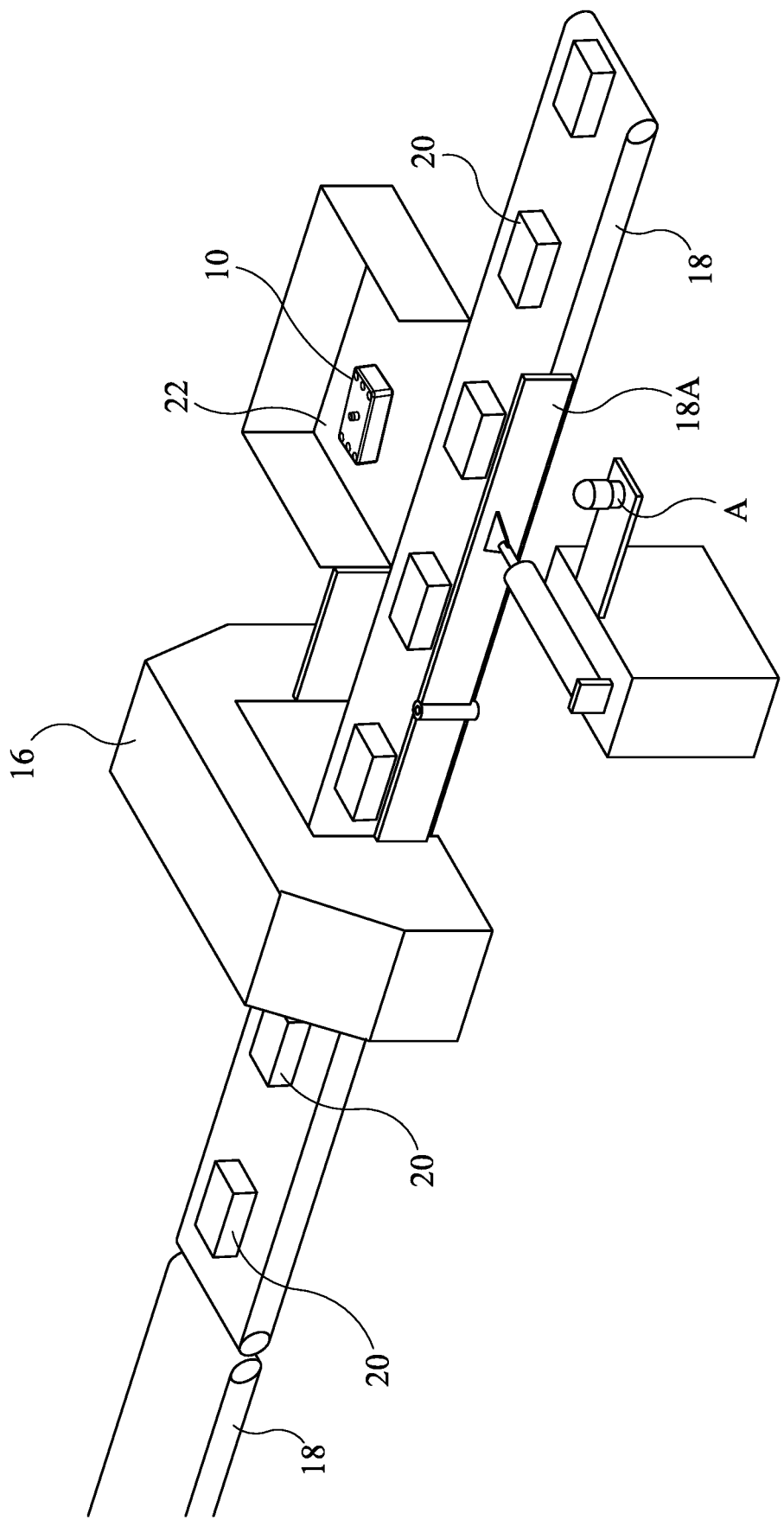
FIG. 9 is yet another further operational view of the assembly line with the exemplary manufacturing test block having been removed from the flow of the line and the remainder of the line continuing uninterrupted.

Referring specifically to FIG. 9, yet another further operational view of the assembly line 18 with the exemplary manufacturing test block 10 having been removed from the flow of the line 18 and the remainder of the line 18 continuing uninterrupted. The device 10 has been removed but other packages are allowed to move on. Prior art methods have caused a real package to be removed, or have caused additional packages to be removed as the detector arm may not be well calibrated. The device 10 along with varying the location of the plug 12 with the test piece 12F inside of it is alone to be removed from the line, rather than catching other collateral packages.

Various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected," "attached" or "coupled" to another feature or element, it can be directly connected, attached or coupled to the other feature or element or intervening features or elements may be present. In contrast, when a feature or element is referred to as being "directly connected," "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Spatially relative terms, such as "under," "below," "lower," "over," "upper," "above," "behind," "in front of," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly," "downwardly," "vertical," "horizontal," "lateral," "transverse," "longitudinal," and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed herein could be termed a second feature/element, and similarly, a second feature/element discussed herein could be termed a first feature/element without departing from the teachings of the present invention.

An embodiment is an implementation or example of the present disclosure. Reference in the specification to "an embodiment," "one embodiment," "some embodiments," "one particular embodiment," "an exemplary embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," "an exemplary embodiment," or "other embodiments," or the like, are not necessarily all referring to the same embodiments.

If this specification states a component, feature, structure, or characteristic "may," "might," or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additionally, the method of performing the present disclosure may occur in a sequence different than those described herein. Accordingly, no sequence of the method should be read as a limitation unless explicitly stated. It is recognizable that performing some of the steps of the method in a different order could achieve a similar result.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed:

1. A manufacturing test block for testing and calibrating a detector provided adjacent a conveyor, wherein the detector is actuatable to detect a contaminant material or substance, said test block comprising:
   a body;
   at least one aperture defined in the body, wherein the at least one aperture extends from an opening defined in an exterior surface of the body to a bottom surface located a distance inwardly from the exterior surface;
   at least one plug configured to interface with the at least one aperture;
   wherein each plug of the at least one plug includes a bottom wall and a side wall extending outwardly from the bottom wall;
   a recess defined in the plug, said recess being bounded and defined by an inner surface of the side wall and an inner surface of the bottom wall; and
   at least one test piece is insertable into the recess of the plug, wherein the at least one test piece is at least partially comprised of the contaminant material or substance.

2. The manufacturing test block of claim 1, wherein the body comprises at least one of the following: acrylonitrile butadiene styrene (ABS), polylactic acid (PLA), acrylonitirle styrene acrylate (ACA), polyethylene terephthalate (PET), glycolized polyester (PETG), polycarbonate (PC), polyetherimide (PEI), polyaryletherketone (PAEK), polyether ether ketone (PEEK), polyetherketoneketone (PEKK), polyphenylsulfone (PPSU), polypropylene (PP), polyamides (nylon), composite materials, and hybrid materials.

3. The manufacturing test block of claim 1, wherein the at least one plug comprises at least one of the following: acrylonitrile butadiene styrene (ABS), polylactic acid (PLA), acrylonitirle styrene acrylate (ACA), polyethylene terephthalate (PET), glycolized polyester (PETG), polycarbonate (PC), polyetherimide (PEI), polyaryletherketone (PAEK), polyether ether ketone (PEEK), polyetherketoneketone (PEKK), polyphenylsulfone (PPSU), polypropylene (PP), polyamides (nylon), thermoplastic polyurethane (TPU), composite materials, and hybrid materials.

4. The manufacturing test block of claim 1, wherein the at least one test piece comprises at least one of the following: chrome steel, brass, stainless steel, titanium, phosphor bronze, and aluminum.

5. The manufacturing test block of claim 1, wherein the at least one test piece comprises at least one of the following: ceramic, soda lime glass, borosilicate glass, crystal glass, polytetrafluoroethylene, nylon, and nitrile.

6. The manufacturing test block of claim 1, wherein the at least one plug is in removable engagement within a first aperture of the at least one aperture defined in the body.

7. The manufacturing test block of claim 1, wherein a first aperture of the at least one aperture is located on a top of the body and a second aperture of the at least one aperture is located on a different side of the body from the top.

8. The manufacturing test block of claim 1, wherein the at least one aperture comprises a first aperture and a second aperture, and wherein the first aperture is of a first depth into the body of the test block and the second aperture is of a second depth into the body of the test block, wherein the second depth is different from the first depth.

9. The manufacturing test block of claim 1, wherein the at least one aperture comprises a first aperture and a second aperture, and wherein the first aperture is of a first diameter and the second aperture is of a second diameter, and the second diameter is different from the first diameter.

10. A method for testing for a contaminant comprising:
    providing a test block comprising a body, an aperture defined in the body, said aperture extending from an opening defined in an exterior surface of the body to a bottom surface located a distance inwardly from the exterior surface;
    providing a plug configured to interface with the aperture, wherein the plug includes a bottom wall and a side wall extending outwardly from the bottom wall;
    defining a recess in the plug, wherein said recess is bounded and defined by an inner surface of the side wall and an inner surface of the bottom wall;
    placing a test piece into the recess of the plug, wherein the test piece is at least partially comprised of the contaminant;
    installing the plug into the aperture of the test block;
    passing the test block through a detector operative to detect the contaminant; and
    detecting the contaminant within the recess of the plug installed in the test block with the detector.

11. The method of claim 10, further comprising:
    removing the plug;
    providing a second plug configured to interface with the aperture of the body, wherein the second plug defines a recess therein which is bounded and defined by an inner surface of a side wall of the second plug and an inner surface of a bottom wall of the second plug;
    placing a second test piece into the recess of the second plug, wherein the second test piece is at least partially comprised of a second contaminant;
    installing a second plug into the aperture of the test block;
    passing the test block through the detector, wherein the detector is further operative to detect the second contaminant; and
    detecting the second contaminant within the recess of the second plug installed in the test block with the detector.

12. The method of claim 10, further comprising:
    providing a plurality of apertures on the body of the test block;
    moving the plug from a first aperture of the plurality of apertures to a second aperture of the plurality of apertures;
    passing the test block through the detector operative to detect the contaminant; and
    detecting the contaminant with the detector.

13. The method of claim 12, further comprising:
    iteratively moving the plug from one aperture to another aperture of the plurality of apertures in order to detect the contaminant at any location within the test block.

14. The method of claim 10, prior to placing further comprising:
    customizing one or more of a shape, size and weight of the test block to a product to be moved along a conveyor adjacent the detector.

15. The method of claim 14, after detecting further comprising:
    changing dimensions of the test block to result in a second test block;
    installing the plug in the second test block;
    passing the second test block through the detector; and
    detecting the contaminant with the detector.

16. The method of claim 10, further comprising:
placing the test block on a conveyor system adjacent the detector.

17. A method for calibrating a detector with a test block comprising:
providing the test block comprising a body, a plurality of apertures defined in the body, each aperture of the plurality of apertures extending from an opening defined in an exterior surface of the body to a bottom surface located a distance inwardly from the exterior surface;
providing a plug including a bottom wall and a side wall extending outwardly from the bottom wall;
defining a recess in the plug, wherein said recess is bounded and defined by an inner surface of the side wall and an inner surface of the bottom wall;
placing a test piece into the recess of the plug, wherein the test piece is at least partially comprised of the contaminant;
installing the plug in a first aperture of the plurality of apertures of the test block;
passing the test block through the detector which is operative to detect the contaminant;
detecting the contaminant in the test block with the detector;
removing the plug from the first aperture;
installing the plug in a second aperture of the plurality of apertures of the test block;
passing the device through the detector; and
detecting the contaminant in the test block with the detector.

18. The method of claim 17, further comprising:
removing the plug from the test block;
installing a second plug within the test block, wherein the second plug includes a bottom wall and a side wall extending outwardly from the bottom wall, and wherein the second plug defines a recess which is bounded and defined by an inner surface of the side wall of the second plug and an inner surface of the bottom wall of the second plug;
placing a second test piece into the recess of the second plug, wherein the second test piece at least partially comprises a second contaminant;
passing the test block through the detector, wherein the detector is operative to detect the second contaminant; and
detecting the second contaminant with the detector.

19. The test block according to claim 1, further comprising indicia provided on region of an outer wall of the at least one plug, said indicia identifying the contaminant present in the test piece received within the recess of the at least one plug.

20. The test block according to claim 1, wherein the side wall of the at least one plug includes:
a first annular region provided proximate a first end of the at least one plug;
a second annular region spaced a distance away from the first annular region;
wherein the first annular region includes a gripping surface; and
wherein the second annular region includes threads configured to matingly engage with threads provided on an inner surface of the test block that defines the at least one aperture.

* * * * *